US011013843B2

(12) United States Patent
Gerber et al.

(10) Patent No.: US 11,013,843 B2
(45) Date of Patent: May 25, 2021

(54) PERITONEAL DIALYSIS FLUID TESTING SYSTEM

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 6 days.

(21) Appl. No.: 15/914,791

(22) Filed: Mar. 7, 2018

(65) Prior Publication Data

US 2018/0193546 A1    Jul. 12, 2018

Related U.S. Application Data

(63) Continuation-in-part of application No. 15/677,261, filed on Aug. 15, 2017.
(Continued)

(51) Int. Cl.
*A61M 1/28* (2006.01)
*A61M 1/16* (2006.01)
(Continued)

(52) U.S. Cl.
CPC ......... *A61M 1/28* (2013.01); *A61B 5/14507* (2013.01); *A61B 5/6866* (2013.01); *A61M 1/1601* (2014.02); *A61M 1/1609* (2014.02); *A61M 1/287* (2013.01); *A61M 2205/3306* (2013.01); *A61M 2205/3324* (2013.01);
(Continued)

(58) Field of Classification Search
CPC ...... A61M 1/28; A61M 1/1609; A61M 1/287; A61M 1/1601; A61M 2205/3306; A61M 2205/3324; A61M 2205/75; A61M 2205/50; A61B 5/6866; A61B 5/14507; G01N 2021/7773; G01N 2800/06; G01N 2021/7783; G01N 2021/7786; G01N 21/80; G01N 21/78
See application file for complete search history.

(56) References Cited

U.S. PATENT DOCUMENTS 2,002 A    3/1841  Rider
3,602,222 A    8/1971  Herndon
(Continued)

FOREIGN PATENT DOCUMENTS

CN    1643368 A    7/2005
CN    101193667    6/2008
(Continued)

OTHER PUBLICATIONS

Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
European Search Report for App. No. 17190053.3, dated Jan. 2, 2018.
European Search Report for App. No. 17190066, dated Jan. 16, 2018.
(Continued)

*Primary Examiner* — Samuel P Siefke (57) ABSTRACT

The invention relates to a testing system and related methods for detecting peritonitis or infection in peritoneal dialysate removed from a patient. The testing system can include a fluid sensor apparatus in a fluid line of a peritoneal dialysis cycler through which spent peritoneal dialysate can be pumped. The fluid sensor apparatus can detect one or more markers associated with peritonitis or infection.

11 Claims, 4 Drawing Sheets

Related U.S. Application Data (60) Provisional application No. 62/385,946, filed on Sep. 9, 2016.

(51) Int. Cl.
  *A61B 5/145* (2006.01)
  *A61B 5/00* (2006.01)
  *G01N 21/78* (2006.01)
  *G01N 21/80* (2006.01)
  *G01N 21/77* (2006.01)

(52) U.S. Cl.
  CPC ..... *A61M 2205/50* (2013.01); *A61M 2205/75* (2013.01); *G01N 21/78* (2013.01); *G01N 21/80* (2013.01); *G01N 2021/7773* (2013.01); *G01N 2021/7783* (2013.01); *G01N 2021/7786* (2013.01); *G01N 2800/06* (2013.01)

(56) References Cited

U.S. PATENT DOCUMENTS

| | | |
|---|---|---|
| 3,608,729 A | 9/1971 | Haselden |
| 3,669,878 A | 6/1972 | Marantz |
| 3,669,880 A | 6/1972 | Marantz |
| 3,730,183 A | 5/1973 | Goldsmith |
| 3,754,867 A | 8/1973 | Guenther |
| 3,850,835 A | 11/1974 | Marantz |
| 3,884,808 A | 5/1975 | Scott |
| 3,989,622 A | 11/1976 | Marantz |
| 3,989,625 A | 11/1976 | Mason |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,661,246 A | 4/1987 | Ash |
| 4,678,408 A | 7/1987 | Mason |
| 4,685,903 A | 8/1987 | Cable |
| 4,747,822 A | 5/1988 | Peabody |
| 4,750,494 A | 6/1988 | King |
| 4,772,560 A | 9/1988 | Attar |
| 4,799,493 A | 1/1989 | DuFault |
| 4,826,663 A | 5/1989 | Alberti |
| 4,828,693 A | 5/1989 | Lindsay |
| 4,976,683 A | 12/1990 | Gauthier |
| 5,032,265 A | 7/1991 | Jha |
| 5,080,653 A | 1/1992 | Voss |
| 5,091,642 A | 2/1992 | Chow |
| 5,092,886 A | 3/1992 | Dobos-Hardy |
| 5,097,122 A | 3/1992 | Coiman |
| 5,127,404 A | 7/1992 | Wyborny |
| 5,141,493 A | 8/1992 | Jacobsen |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,364,593 A | 11/1994 | Mihaylov |
| 5,468,388 A | 11/1995 | Goddard |
| 5,507,723 A | 4/1996 | Keshaviah |
| 5,643,201 A | 7/1997 | Peabody |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,819,007 A | 10/1998 | Elghazzawi |
| 5,902,336 A | 5/1999 | Mishkin |
| 5,944,684 A | 8/1999 | Roberts |
| 5,987,352 A | 11/1999 | Klein |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,645,191 B1 | 11/2003 | Knerr |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,207,946 B2 | 4/2007 | Sirokman |
| 7,208,092 B2 | 4/2007 | Micheli |
| 7,276,042 B2 | 10/2007 | Polaschegg |
| 7,399,289 B2 | 7/2008 | Gelfand |
| 7,404,799 B1 | 7/2008 | Koh |
| 7,500,958 B2 | 3/2009 | Asbrink |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,775,986 B2 | 8/2010 | Roeher |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |

(56) References Cited

U.S. PATENT DOCUMENTS

| | | |
|---|---|---|
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 9,907,897 B2 | 3/2018 | Burbank |
| 2001/0048637 A1 | 12/2001 | Weigl |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 2/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | TranThong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0149776 A1 | 6/2009 | Adams |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010425 A1 | 1/2010 | Yu |
| 2010/0010429 A1 | 1/2010 | Childers |
| 2010/0042035 A1 | 2/2010 | Moissl |
| 2010/0061892 A1 | 3/2010 | Flaim |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |

(56) References Cited

U.S. PATENT DOCUMENTS

| | | |
|---|---|---|
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | QiAn |
| 2013/0168316 A1 | 7/2013 | Noguchi |
| 2013/0186759 A1 | 7/2013 | Lin |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0276100 A1 | 9/2014 | Satterfield |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0023467 A1 | 1/2016 | Din et al. |
| 2016/0143774 A1 | 5/2016 | Burnett |
| 2016/0206801 A1 | 7/2016 | Gerber |
| 2016/0331884 A1 | 11/2016 | Sigg |
| 2018/0043080 A1 | 2/2018 | Gerber |

FOREIGN PATENT DOCUMENTS

| | | |
|---|---|---|
| CN | 101300476 A | 11/2008 |
| CN | 101400997 | 1/2009 |
| CN | 101482572 | 7/2009 |
| CN | 202048893 | 3/2011 |
| CN | 103037917 | 4/2013 |
| CN | 103439230 A | 9/2013 |
| CN | 103803479 | 5/2014 |
| CN | 104833635 A | 8/2015 |
| CN | 105008893 B | 10/2015 |
| CN | 105115921 | 12/2015 |
| CN | 105928939 | 7/2016 |
| CN | 101644667 | 2/2020 |
| DE | 3224823 | 1/1984 |
| EP | 266795 A2 | 11/1987 |
| EP | 0402505 | 12/1990 |
| EP | 0272414 | 10/1991 |
| EP | 0330892 | 7/1994 |
| EP | 1124599 | 5/2000 |
| EP | 1175238 | 11/2000 |
| EP | 1281351 | 2/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | S551980138462 | 10/1980 |
| JP | S63-143077 | 11/1987 |
| JP | 2002533170 | 10/2002 |
| JP | 2002542900 | 12/2002 |
| JP | 2003235965 | 8/2003 |
| JP | 2005-533573 | 11/2005 |
| JP | 5099464 | 10/2012 |
| WO | 1995003839 | 2/1995 |
| WO | WO 1998054563 | 12/1998 |
| WO | WO1999006082 | 2/1999 |
| WO | 9937342 | 7/1999 |
| WO | 0057935 | 10/2000 |
| WO | WO2000057935 A1 | 10/2000 |
| WO | 200066197 A1 | 11/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 1085295 | 11/2001 |
| WO | 2002013691 | 2/2002 |
| WO | WO 20020053211 | 7/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 20070115321 | 10/2007 |
| WO | WO2009094035 A1 | 1/2008 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | WO2009154955 A2 | 12/2009 |
| WO | WO 20099154955 | 12/2009 |
| WO | WO 20100002830 | 1/2010 |
| WO | 2010024963 | 3/2010 |
| WO | 2010028860 | 3/2010 |
| WO | 2010028860 A1 | 3/2010 |

(56) References Cited

FOREIGN PATENT DOCUMENTS

| WO | 2010033314 | 3/2010 |
|---|---|---|
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO2013022760 A1 | 8/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | WO 2012/129501 | 9/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 20120277551 | 11/2012 |
| WO | WO2012148788 A1 | 11/2012 |
| WO | WO 20120148784 | 11/2012 |
| WO | 2012148784 | 12/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013101292 A3 | 10/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2014121161 | 8/2014 |
| WO | WO 20140121161 | 8/2014 |
| WO | WO 20140121169 | 8/2014 |
| WO | WO2015081221 A1 | 6/2015 |
| WO | WO 20150130205 | 9/2015 |
| WO | WO 20150159280 | 10/2015 |
| WO | WO 20160080883 | 5/2016 |
| WO | WO 20170034452 | 3/2017 |
| WO | WO 2017/176687 | 10/2017 |
| WO | WO 2017/176701 | 10/2017 |

OTHER PUBLICATIONS

European Search Report for App. No. 17190084, dated Feb. 9, 2018.
[NPL326] PCT/US2014/065201 International Search Report dated May 26, 2015.
[NPL328] Genovesi, et al., Nephrology, Dialysis, Transplantation 2009; 24(8):2529-2536.
[NPL32] Secemsky, et. al, High prevalence of cardiac autonomic dysfunction and T-wave alternans in dialysis patients. Heart Rhythm, Apr. 2011, 592-598 : vol. 8, No. 4.
[NPL339] U.S. Appl. No. 13/424,517 IDS, filed Aug. 2, 2012.
[NPL340] U.S. Appl. No. 13/424,517, IDS filed Dec. 2, 2013.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225, filed Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.
[NPL46] Siegenthaler, et al., Pulmonary fluid status monitoring with intrathoracic impedance, Journal of Clinical Monitoring and Computing, 24:449-451, published Jan. 12, 2011.
[NPL477] Office Action in U.S. Appl. No. 13/757,792 dated Apr. 6, 2015.
[NPL47] U.S. Appl. No. 61/480,544.
[NPL483] Office Action in U.S. Appl. No. 13/424,525 dated Aug. 11, 2015.
[NPL486] Office Action in U.S. Appl. No. 13/424,525 dated Oct. 20, 2016.
[NPL494] John Wm Agar: Review: Understanding sorbent dialysis systems, Nephrology, vol. 15, No. 4, Jun. 1, 2010, pp. 406-411.
[NPL495] European Office Action in Application 12717020.7 dated Sep. 14, 2016.
[NPL500] Office Action in U.S. Appl. No. 14/554,272 dated Aug. 8, 2016.
[NPL501] Office Action in U.S. Appl. No. 13/424,467 dated Oct. 16, 2013.
[NPL502] Office Action in U.S. Appl. No. 13/424,467 dated Mar. 3, 2014.
[NPL503] Office Action in U.S. Appl. No. 13/424,490 dated Oct. 22, 2013.
[NPL504] Office Action in U.S. Appl. No. 13/424,490 dated Mar. 10, 2014.
[NPL505] Office Action in U.S. Appl. No. 13/424,490 dated Jul. 14, 2014.
[NPL506] Office Action in U.S. Appl. No. 13/424,490 dated Dec. 5, 2014.
[NPL507] Office Action in U.S. Appl. No. 13/424,525 dated Sep. 29, 2014.
[NPL508] Office Action in U.S. Appl. No. 13/424,525 dated May 6, 2015.
[NPL509] Office Action in U.S. Appl. No. 13/424,454 dated Oct. 17, 2013.
[NPL510] Office Action in U.S. Appl. No. 13/424,454 dated Mar. 10, 2014.
[NPL511] Office action in U.S. Appl. No. 13/424,429 dated Oct. 15, 2015.
[NPL512] Office Action in U.S. Appl. No. 12/571,127 dated Feb. 27, 2014.
[NPL513] Office Action in U.S. Appl. No. 12/571,127 dated Jul. 6, 2015.
[NPL514] Office Action in U.S. Appl. No. 12/571,127 dated Dec. 17, 2015.
[NPL521] Office Action in U.S. Appl. No. 14/554,338 dated Jun. 7, 2016.
[NPL522] Office Action in U.S. Appl. No. 14/554,338 dated Sep. 28, 2016.
[NPL524] Office Action in U.S. Appl. No. 13/424,429 dated Oct. 15, 2015.
[NPL525] Office Action in U.S. Appl. No. 12/571,127 dated Feb. 27, 2014.
[NPL526] Office Action in U.S. Appl. No. 12/571,127 dated Jul. 6, 2015.

(56) References Cited

OTHER PUBLICATIONS

[NPL527] Office Action in U.S. Appl. No. 12/571,127 dated Dec. 17, 2015.
[NPL539] Office Action in U.S. Appl. No. 12/571,127 dated Nov. 8, 2012.
[NPL540] Office Action in U.S. Appl. No. 14/554,338 dated Jun. 7, 2016.
[NPL541] Office Action in U.S. Appl. No. 14/554,338 dated Sep. 28, 2016.
[NPL542] Office Action in U.S. Appl. No. 14/554,272 dated Aug. 8, 2016.
[NPL543] Office Action in U.S. Appl. No. 13/424,479 dated Oct. 25, 2014.
[NPL545] Office Action in U.S. Appl. No. 14/566,686 dated Apr. 28, 2016.
[NPL547] Office Action in Chinese Application No. 201510511657.9 dated Dec. 28, 2016.
[NPL55] U.S. Appl. No. 13/424,454.
[NPL57] U.S. Appl. No. 13/424,467.
[NPL582] Office Action in U.S. Appl. No. 13/757,792 dated Apr. 6, 2015.
[NPL62] U.S. Appl. No. 13/424,533.
[NPL632] Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL633] Gordhandas et al, Real-Time Extraction and Analysis of Key Morphological Features in the Electrocardiogram, for Data Compression and Clinical Decision Support, 2004, Computational Physiology, pp. 15-18.
[NPL671] European Office Action in Application 12717020.7 dated Dec. 11, 2015.
[NPL672] PCT/US2012/034331 International Preliminary Report on Patentability and Written Opinion dated Oct. 29, 2013.
[NPL674] Office Action in Chinese Application No. 201280020932.1 dated Jan. 7, 2015.
[NPL675] Office Action in Chinese Application No. 201280020932.1 dated Apr. 3, 2015.
[NPL67] U.S. Appl. No. 13/424,490.
[NPL68] U.S. Appl. No. 13/424,517.
[NPL693] PCT/US2012/034330, International Search Report and Written Opinion dated Aug. 28, 2012.
[NPL699] Office Action in Chinese Application No. 201280020937.4 dated Oct. 22, 2016.
[NPL700] Office Action in Japanese Application No. 2014-508434 dated Nov. 16, 2015.
[NPL701] Office Action in Japanese Application No. 2014-508434 dated Dec. 8, 2014.
[NPL702] Office Action in Japanese Application No. 2014-508434 dated Nov. 4, 2016.
[NPL703] Office Action in European Application No. 12717019.9 dated Feburary 16, 2017.
[NPL706] Office Action in Chinese Application No. 201510511657.9 dated May 10, 2017.
[NPL709] PCT/US2014/065201 International Preliminary Report on Patentability dated May 19, 2016.
[NPL727] Office Action in European Application No. EP 12717021.5 dated Feb. 3, 2017.
[NPL735] Office Action in Chinese Application No. 201510593695.3 dated Jul. 12, 2017.
[NPL748] Office Action in European Application No. EP 12719170.8 dated Jan. 14, 2015.
[NPL749] Office Action in Japanese Application No. JP 2014-508437 dated Dec. 8, 2014.
[NPL757] U.S. Appl. No. 60/650,497, filed Feb. 7, 2005.
[NPL81] U.S. Appl. No. 61/480,539, filed Apr. 29, 2011.
[NPL84] U.S. Appl. No. 61/480,535, filed Apr. 29, 2011.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, dated Jun. 12, 2017.
[NPL] European Search Report for Application No. 14865128.4 dated Jun. 20, 2017.
[NPL] Green et al., Sudden Cardiac Death in Hemodialysis Patients: an In-Depth Review , Am J Kidney Dis 57(6)921:929.
[NPL] Rajan et al. Generalized Feature Extraction for Time-Varying Autoregressive Models, IEEE Transacion Signal Processing vol. 44, No. 10.
Castellanos, et al, Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese Office Action in App. No. 201480059332.5, dated Mar. 30, 2018.
Dejardin, et al, Intraperitoneal pressure in PD patients: relationship to intraperitoneal volume, body size and PD-related complications, Nephrol Dial Transplant. May 2007;22(5):1437-44.
European Search Report for App. No. 17185636.2, dated Mar. 27, 2018.
European Search Report for App. No. 14859115.9, dated Jan. 5, 2018.
European Search Report for App. No. 17185636.2 dated Jan. 10, 2018.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
PCT/US2016/058579 International Search Report dated Jan. 31, 2017.
PCT/US2016/058579_WO.
PCT/US2017/025868 International Search Report dated Jun. 29, 2017.
PCT/US2017/025868 Written Opinion dated Jun. 29, 2017.
PCT/US2017/030377_ISR.
PCT/US2017/030377_WO.
PCTUS20170146199 ISR and written opinion, dated Feb. 19, 2018.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Written Opinion in Dutch App. No. 2018577, dated Nov. 2, 2017.
International Preliminary Report on Patentability for App. No. PCT/US2019/019334, dated Jun. 12, 2019.
Office Action in Chinese App. No. 201710778666.3 dated Sep. 19, 2019.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541, filed Apr. 29, 2011.

(56) References Cited

OTHER PUBLICATIONS

[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL14] Foley, et al., Long Interdialytic Interval and Martality among Patients Receiving Hemodialysis, N Engl Jrnl Med. 2011:365(12):1099-1107.
[NPL15] PCT International Search Report from International Application No. PCT/US2014/067650, dated Nov. 27, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al, Kidney International. Jun. 2006; 69(12):2268-2273.
[NPL176] Bleyer, et. al., Sudden and cardiac death rated in hemodialysis patients, Kidney International. 1999, 1553-1559: 55.
[NPL180] PCT/US2012/034335, International Preliminary Report on Patentability, dated Nov. 7, 2013.
[NPL181] PCT/US2012/034303, Internationa Search Report, dated Jul. 6, 2013.
[NPL186] PCT/US2012/034332, Internatonal Preliminary Report on Patentability, dated Oct. 29, 2013.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL195] PCT/US2012/034327, International Preliminary Report on Patentability, dated Oct. 29, 2013.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479, filed Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429, filed Nov. 1, 2012.
[NPL230] Redfield, et. al, Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL233] PCT/US2012/034329, International Preliminary Report on Patentability, dated Oct. 29, 2013.
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, filed Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. p. 280: R48-R55, Jan. 1, 2001.
[NPL27] Overgaard. et. al., Relations between excitability and contractility in rate soleusmuscle: role of the NA+-K+ pump and NA+-K—S gradients. Journal of Physiology, 1999, 215-225, 518(1).
[NPL285] Zoccali, Pulmonary Congestion Predicts Cardiac Events and Mortality in ESRD, Clinical Epidemiology, J. Am Soc Nephrol 24:639-646, 2013.
[NPL306] Coast, et al. 1990, An approach to Cardiac Arrhythmia analysis Using Hidden Markov Models, IEEE Transactions On Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL310] U.S. Appl. No. 61/480,532.
[NPL311] U.S. Appl. No. 13/424,479.
[NPL312] U.S. Appl. No. 13/424,429, filed Nov. 1, 2012.
[NPL313] U.S. Appl. No. 13/424,525.
[NPL317] U.S. Appl. No. 61/480,530.
[NPL318] U.S. Appl. No. 61/480,528, filed Apr. 29, 2011.
[NPL322] Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
[NPL323] Whitman, CKD and Sudden Cardiac Death: Epidemiology, Mechanisms, and Therapeutic Approaches, J Am Soc Nephrol, 23:1929-1939, 2012.
[NPL324] Hall, Hospitalization for Congestive Heart Failure: United States, 2000-2010, NCHS Data Brief, No. 108, Oct. 2012.
[NPL325] Albert, Fluid Management Strategies in Heart Failure, Critical Care Nurse, 32:20-32, 2012.
Chinese Office Action for App. No. 201710778666.3, dated Jul. 15, 2020.
Chinese Office Action for App. No. 2019071601874110, dated Jul. 19, 2019.
European Office Action for App. No. 17190053.3, dated Sep. 18, 2019.
European Search Report for App. No. 17190081.4, dated Sep. 16, 2019.
Henderson, et al, "Online Preparation of Sterile Pyrogen-Free Electrolyte Solution," Trans. Am. Soc. Artif.Intern.Organs, 1978 pp. 465-467.
Indian OA of Nov. 21, 2019 in 2981/KOLNP/2013.
Schmitt, et al, "Colorimetric Gas Sensing with Enhanced Sensitivity," Procedia Engineering, vol. 168, Sep. 3, 2016, pp. 1237-1240.
Chinese Office Action for App. No. 201710779349.3, dated Jun. 1, 2020.
Chinese Office Action for App. No. 201710779964.4, dated Apr. 14, 2020.
Chinese Office Action for App. No. 201710779964.4, dated Aug. 26, 2020.
European Search for App. No. 17190081.4, dated Feb. 5, 2021.
Chinese Office Action for App. No. 201710778666.3, dated Nov. 20, 2020.

PERITONEAL DIALYSIS FLUID TESTING SYSTEM

FIELD OF THE INVENTION

The invention relates to a testing system and related methods for detecting peritonitis or infection in peritoneal dialysate removed from a patient. The testing system can include a fluid sensor apparatus in a fluid line of a peritoneal dialysis cycler through which spent peritoneal dialysate can be pumped. The fluid sensor apparatus can detect one or more markers associated with peritonitis or infection.

BACKGROUND

Peritoneal Dialysis (PD), including Automated Peritoneal Dialysis (APD) and Continuous Ambulatory Peritoneal Dialysis (CAPD), is a dialysis treatment that can be performed at home, either by the patient alone or with a care-giver. PD differs from Hemodialysis (HD) in that blood is not removed from the body and passed through a dialyzer, but rather a catheter is placed in the peritoneal cavity and dialysate introduced directly into the peritoneal cavity. Blood is cleaned inside the patient using the patient's own peritoneum as a type of dialysis membrane. However, because fluid is directly introduced into a human body, the fluid used for peritoneal dialysate is generally required to be free of biological and chemical contaminants. Due to the risk of infection by PD patients, continuous monitoring is required.

Current methods of diagnosing peritonitis or infection in PD patients involves the patient checking the used peritoneal dialysate for cloudiness or discoloration, and if the used peritoneal dialysate is cloudy or discolored, testing the used peritoneal dialysate at a clinic. Cloudiness or discoloration, however, can have several causes other than infection, and as such, the current methods result in many false positives, leading to expensive testing and treatment of otherwise healthy individuals. Testing can increase the time between the onset of infection and the beginning of treatment for the infection. Visual inspection and other known means of testing may not be dispositive.

Hence, there is a need for systems and methods that can test spent peritoneal dialysate for infection or peritonitis without the need to send the spent peritoneal dialysate to a clinic. There is a further need for systems and methods that can automatically, accurately, and correctly test and analyze the spent peritoneal dialysate, eliminating the need for individual patients to conduct visual inspections. The need extends to systems and methods that can quickly and dispositively determine whether a patient has peritonitis or an infection.

SUMMARY OF THE INVENTION

The first aspect of the invention is drawn to a system. In any embodiment, the system can comprise a peritoneal dialysis cycler; the peritoneal dialysis cycler comprising a catheter for removing peritoneal dialysate from a patient, at least one fluid line fluidly connected to the catheter; a pump; and a fluid sensor apparatus; the fluid sensor apparatus fluidly connected to the fluid line; the fluid sensor apparatus detecting at least one fluid characteristic in fluid removed from the patient; and a processor, the processor programmed to identify peritonitis and/or infection based on the at least one fluid characteristic.

In any embodiment, at least one fluid characteristic can comprise at least one marker correlated with peritonitis and/or infection.

In any embodiment, the fluid sensor apparatus can comprise: at least one fluid inlet fluidly connected to the fluid line and at least one fluid outlet fluidly connected to a second fluid line; a receiving slot for a sensor card; the receiving slot fluidly connected to the fluid inlet and fluid outlet; a light source directing light onto a first side of the sensor card; and a camera or photodetector detecting light on a second side of the sensor card opposite to the first side of the sensor card; the camera or photodetector in communication with a processor, the processor programmed to identify peritonitis and/or infection based on the at least one fluid characteristic.

In any embodiment, the sensor card can comprise at least one sensor region; the at least one sensor region undergoing a detectable change in response to at least one marker correlated with peritonitis and/or infection.

In any embodiment, the sensor card can comprise at least two sensor regions; wherein a first sensor region undergoes a detectable change in response to a first marker correlated with peritonitis and/or infection; and wherein a second sensor region undergoes a detectable change in response to a second marker correlated with peritonitis and/or infection.

In any embodiment, the at least one marker can be selected from a group consisting of MMP8, IL-6, HNE, MMP2, MMP9, TIMP1, TIMP2, NGAL, A1AT, desmosine, fibrinogen, IL-8, calprotectin, fMLP, IL1 b, cystatin C, HSA, RBP4, SPD, MPO, sICAM and TNFa.

In any embodiment, the system can comprise a bypass line fluidly connecting the fluid line upstream of the fluid sensor apparatus to the second fluid line downstream of the fluid sensor apparatus.

In any embodiment, the second fluid line can be fluidly connected to a drain and/or to a waste reservoir.

In any embodiment, the catheter can be a dual lumen catheter.

In any embodiment, the catheter can comprise at least one side slot.

In any embodiment, the at least one fluid characteristic can comprise at least one of a color and/or a clarity of the fluid.

Any of the features disclosed as being part of the first aspect of the invention can be included with any other feature of the first aspect of the invention, either alone or in any combination or sub-combination with the other features.

The second aspect of the invention is drawn to a method. In any embodiment, the method can comprise pumping a peritoneal dialysate from a peritoneal cavity of a patient through a catheter to a fluid sensor apparatus; and detecting at least one fluid characteristic of the peritoneal dialysate correlated with peritonitis and/or infection.

In any embodiment, the fluid sensor apparatus can comprise at least one fluid inlet fluidly connected to the catheter and at least one fluid outlet fluidly connected to a second fluid line; wherein fluid is pumped through the fluid sensor apparatus from the inlet to the outlet; a receiving slot for a sensor card; the receiving slot in fluid communication with the fluid inlet and fluid outlet; a light source directing light onto a first side of the sensor card; and a camera or photodetector detecting light on a second side of the sensor card opposite to the first side of the sensor card; wherein the step of detecting at least one fluid characteristic of the peritoneal dialysate comprises the steps of directing light from the light source onto a first side of the sensor card and detecting the light on a second side of the sensor card.

In any embodiment, peritoneal dialysate can be pumped from the peritoneal cavity of the patient through the fluid sensor apparatus during a dwell period.

In any embodiment, peritoneal dialysate can be pumped from the peritoneal cavity of the patient through the fluid sensor apparatus during a drain portion of a peritoneal dialysis cycle.

In any embodiment, the at least one fluid characteristic can be one or more markers correlated with peritonitis and/or infection.

In any embodiment, the method can comprise the step of diagnosing the patient with peritonitis and/or infection based on the at least one fluid characteristic.

In any embodiment, the step of diagnosing the patient with peritonitis and/or infection can be performed by a processor in communication with the fluid sensor apparatus.

In any embodiment, the one or more markers associated with peritonitis and/or infection can be selected from a group consisting of MMP8, IL-6, HNE, MMP2, MMP9, TIMP1, TIMP2, NGAL, A1AT, desmosine, fibrinogen, IL-8, calprotectin, fMLP, IL1 b, cystatin C, HSA, RBP4, SPD, MPO, sICAM and TNFa.

In any embodiment, the at least one fluid characteristic of the peritoneal dialysate can comprise at least one of a color and a clarity of the fluid.

Any of the features disclosed as being part of the second aspect of the invention can be included with any other feature of the second aspect of the invention, either alone or in any combination or sub-combination with the other features.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

A "bypass line" can be a fluid line in a flow path that can allow fluid or fluid flow in, for example, a main line, to move around or avoid one or more components or portions of the flow path, and then optionally, rejoin the main line.

A "camera" is a component capable of creating a digital representation of light intensity, light composition, or both.

A "catheter" can be any tube or fluid line comprising any number of lumens through which fluids or fluid flow can pass through. The catheter can be used to add or remove fluids or fluid flow from a body of a patient. The catheter can be inserted into a body cavity for introducing or withdrawing fluid of any type. The catheter can be rigid, flexible, or semi-flexible and can be constructed of any suitable material known in the art.

The term "clarity" refers to an amount of radiant light or energy shined on a fluid that can pass through the fluid.

The term "color" refers to a wavelength of light reflected from or transmitted through a component, fluid, substance, compound, or feature.

The terms "communication" or "electronic communication" refer to the ability to transmit electronic information between two components or systems.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "dual lumen catheter" is a catheter having two fluid passageways for moving fluid through the catheter in both directions.

A "detectable change" is any change in color, optical transmittance, or change emitted fluorescent light intensity or wavelength in a sensor region.

The terms "detecting," "detected," or "to detect" refer to determining a state or characteristic of any variable, system, or system. For example, a fluid characteristic or parameter can be detected by a sensor detecting that particular fluid characteristic or parameter.

The term "detecting light" or to "detect light" means to measure a wavelength or intensity of light.

The term "diagnosing" or to "diagnose" means to determine whether a patient has a specified illness or condition.

The term "directing light" or to "direct light" refer to causing light to move in a specified path or to a specified location.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "drain" is a fluid line through which fluids may be disposed.

A "drain portion of a peritoneal dialysis cycle" is a time during peritoneal dialysis during which peritoneal dialysate is removed from the peritoneal cavity of a patient.

The term "dwell period" refers to a time during a peritoneal dialysis cycle wherein peritoneal dialysate is kept within the peritoneal cavity of a patient.

A "fluid" is a liquid substance optionally having a combination of gas and liquid phases in the fluid. Notably, a liquid, as used herein, can therefore also have a mixture of gas and liquid phases of matter.

A "fluid characteristic" is any sensed characteristic of a fluid, including temperature, pressure, concentration, color, or any other characteristic.

The term "fluid inlet" refers to a conduit or opening through which fluid, gas, or a combination thereof, can enter a component or apparatus.

A "fluid line" can refer to a tubing or conduit through which a fluid, gas, or a combination thereof can pass. The fluid line can also contain air during different modes of operation such as cleaning or purging of a line.

The term "fluid outlet" refers to a conduit or opening through which fluid, gas, or a combination thereof, can exit a component or apparatus.

The term "fluid sensor apparatus" refers to an apparatus through which fluid can be pumped to determine any one of a solute, solute concentration, ion concentration, a pH, or a combination of solutes in the fluid.

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

To "identify" a particular state or condition means to ascertain whether that state or condition presently exists.

The term "infection" can refer to any virus, bacteria, or pathogen in a patient's tissue. Infections typically occur due to an invasion and multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic vessels to become systemic. Microorganisms that live naturally in or on the body may not be considered infections. For example, bacteria that normally live within the mouth and intestine may not be infections depending on an immunity state and health of the body. However, if the body's immunity were to be compromised, the naturally occurring microorganisms may become infectious.

A "light source," "light emitter," "photo emitter," or the like, is any component capable of emitting light at any wavelength including visible, infrared, or ultraviolet light.

A "marker correlated with peritonitis and/or infection" can be any substance, chemical, material, or compound wherein the concentration of the substance, chemical, material, or compound can be used to identify peritonitis and/or an infection in a patient. The marker can be generally found in a bodily fluid.

The terms "opposite," "opposing," and "positioned opposedly" refer to relative positions of two or more components wherein the two or more components are positioned substantially on opposite sides to a reference point.

A "patient" or "subject" is a member of any animal species, preferably a mammalian species, optionally a human. The subject can be an apparently healthy individual, an individual suffering from a disease, or an individual being treated for a disease. In certain embodiments, the patient can be a human, sheep, goat, dog, cat, mouse or any other animal.

The term "peritoneal cavity" refers to the space between the parietal peritoneum and visceral peritoneum of a patient.

"Peritoneal dialysate" is a dialysis solution that can be used in peritoneal dialysis having specified parameters for purity and sterility. Peritoneal dialysate is not the same as dialysate used in hemodialysis although peritoneal dialysate may be used in hemodialysis.

A "peritoneal dialysis cycler" can be a component or system for movement of fluid into and out of the peritoneal cavity of a patient. In certain embodiments a peritoneal dialysis cycler can be an integrated cycler, wherein the integrated cycler forms a part of an overall system. For example, the integrated cycler can be contained in a housing with other components used for peritoneal dialysis and be in fluid and electrical connection with desired components. Alternatively, the peritoneal dialysis cycler can be external to systems for generation and disposal of peritoneal dialysate.

The term "peritoneal dialysis cycle" or "cycle" can refer to any one, or combination of infusion of peritoneal dialysate into a patient, a dwell of the peritoneal dialysate within the peritoneal cavity of the patient, and the removal of the peritoneal dialysate from the peritoneal cavity of the patient. The process of filling and then draining your abdomen can be considered an "exchange" of used and clean fluids. However, the number, length, and timing of "cycles" or "exchanges" are nonlimiting. For example, Continuous Ambulatory Peritoneal Dialysis (CAPD) and Continuous Cycling Peritoneal Dialysis (CCPD) may occur on different schedules, but the process of filling and then draining the peritoneal cavity can be referred to as "cycles" for both CAPD and CCPD. As such, the term is "cycle" or exchange refers to any dialysis schedule or type of dialysis.

The term "peritonitis" can refer to an inflammation of the peritoneum.

A "photodetector" is a component capable of detecting light intensity, light composition, or both to result in data, such as an image, of the light detected. The terms "camera" and "photo detector" can also generally refer to any type of detector including an RGB detector or spectrophotometer.

The term "processor" as used is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "programmed," when referring to a processor, can mean a series of instructions that cause a processor to perform certain steps.

The term "pump" refers to any device that causes the movement of fluids or gases by applying suction or pressure.

The terms "pumping," "pumped," or to "pump" refer moving a fluid, gas, or combination thereof, with a pump.

The term "receiving slot" is a space within a component or apparatus into which a second component or apparatus can be placed.

The term "removing fluid" or to "remove fluid" means to withdraw fluid from a reservoir, container, system, or patient.

The term "sensor card" refers to a rigid and/or planar component having at least one sensing membrane or sensing material of any kind disposed on, inside or integral to the "sensor card." The sensing membrane or material can contact a fluid and produce a detectable change in response to a fluid characteristic of the fluid.

A "sensor region" or "sensing region" is a portion of a sensor card that undergoes a detectable change in response to a fluid characteristic.

A "side of a sensor card" is any portion of a sensor card having a surface area. The terms "first side" or "second side" as used when referring to a sensor card, are meant to differentiate between two different sides of the sensor card, and are not meant to further limit the shape or position of the sensor card. In certain embodiments, the first side and the second side of the sensor card can be opposite sides.

A "side slot" is an opening in a catheter, positioned on a side of the catheter to promote flow over a catheter slot surface.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "waste reservoir" is a container into which used or unwanted fluids are stored for later disposal.

Peritoneal Dialysis Fluid Testing

Figure 1:
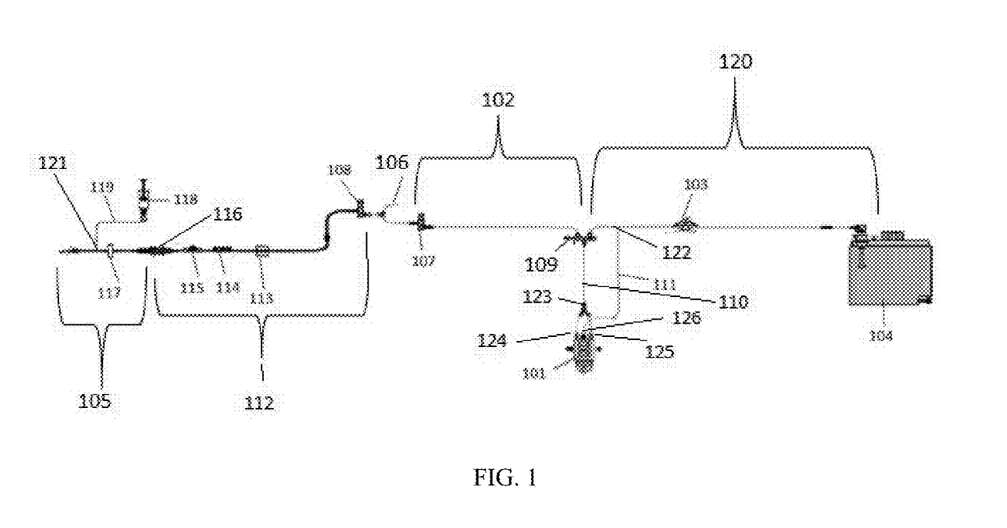
FIG. 1 illustrates a peritoneal dialysis cycler with a fluid sensor apparatus.

FIG. 1 illustrates a peritoneal dialysis cycler with a fluid sensor apparatus 101 for testing peritoneal dialysate effluent. Peritoneal dialysate, which can be generated either by the system or provided in a separated fluid source that is fluidly connectable to the system, is pumped through peritoneal dialysate inlet line 106 by a pump (not shown). The peritoneal dialysate is pumped through valve 108 and cycler line 112 and connector 116 to catheter 105, and then into a patient (not shown). The cycler line 112 can extend from valve 108 to connector 116. A filter 117 can be included to ensure any particulate matter is removed prior to pumping the peritoneal dialysate into the patient. In certain embodiments, one or more additional sensors can be included to sense certain fluid characteristics of the peritoneal dialysate in cycler line 112, including an air detector 113, a flow sensor 114, a pressure sensor 115 and a temperature sensor (not shown). Although shown as sensors arranged in series in FIG. 1, other arrangements of the air detector 113, flow sensor 114, pressure sensor 115 and temperature sensor are contemplated. For example, one or more of the sensors can be arranged in parallel. Alternatively, one or more sensor lines can be included, with a portion of fluid drawn out of the cycler line 112 and passed through any of the sensors. Bypass lines and/or valves can be included to selectively direct the peritoneal dialysate through any of the sensors. Medication, such as heparin, can be added by syringe 118 through fluid line 119. T-junction 121 can provide for medication to flow from fluid line 119 to enter the catheter 105. The T-junction 121 can be replaced by any valve as described herein (not shown) for control over adding medication from syringe 118. After a dwell period the peritoneal dialysate can be removed from the patient through catheter 105 and cycler line 112 back to the valve 108. Pump 103 can provide a driving force for removing fluid from the peritoneal cavity of the patient. Pump 103 can be a bi-directional pump. A bi-directional pump can allow fluid to be pumped from the patient through drain lines 102 and 120 from valve 108 to reservoir 104 or a drain, and also to pump fluid from a reservoir 104 to valve 108.

During draining, valve 108 can be set to direct fluid into drain line 102, which can include valve 107 for fluid control and extend from valve 108 to an optional valve 109. Valve 107 controls the flow of peritoneal dialysate into or out of the drain line 102. Valve 107 can be closed when fluid is being pumped into the cycler line 112 from peritoneal dialysate inlet line 106. Valve 107 can be open when draining fluid from the patient. By selectively opening or closing valve 107, fresh dialysate can be prevented from entering drain line 102. The drain line 102, in certain embodiments, can include optional valve 109, which can selectively direct all or part of the drained peritoneal dialysate through fluid line 110, which includes the fluid sensor apparatus 101. In certain embodiments, only a portion of the spent peritoneal dialysate can be pumped through fluid line 110, with the rest bypassing the fluid line 110 and fluid sensor apparatus 101 through drain line 102. Alternatively, valve 109 can be optional, with the fluid sensor apparatus 101 positioned in the drain line 102 such that all spent peritoneal dialysate passes through the fluid sensor apparatus 101. In other embodiments, an additional bypass line (not shown) can be included, with one or more valves selectively directing fluid through the fluid sensor apparatus 101 or through the bypass line to bypass the fluid sensor apparatus 101 from upstream to downstream of the fluid sensor apparatus 101. Fluid exiting the fluid sensor apparatus 101 can be returned to the drain line 120 through fluid line 111. Drain line 120 can extend from valve 109 to a reservoir 104, or optionally to a drain. In embodiments where the fluid sensor apparatus 101 is in the drain line, the segments of the drain line 102 and 120 can be replaced by a single drain line. The spent dialysate can be pumped to a waste reservoir 104, or alternatively, to a drain (not shown) for disposal. One of skill in the art will understand that the flow path illustrated in FIG. 1 is for illustrative purposes only, and that other arrangement of fluid lines and valves are contemplated by the invention.

As described herein, in certain embodiments the fluid sensor apparatus 101 can include two fluid inlets 124 and 125, and one fluid outlet 126. The two inlets provide an even and complete flow through the fluid sensor apparatus 101. However, a fluid sensor apparatus 101 with a single fluid inlet or with multiple fluid outlets can also be used. Junction 123 can split the peritoneal dialysate in fluid line 110 into two streams, with each stream entering one of the fluid inlets 124 or 125. The fluid outlet 126 is fluidly connectable to fluid line 111, which connects to the drain line 120 at T-junction 122, allowing the fluid sensor apparatus 101 to be isolated from the drain lines 102 and 120.

The catheter 105 can be any type of single or and multi-lumen catheter known in the art. A processor (not shown) can control the timing of sampling of peritoneal dialysate from the patient, as well as identification of peritonitis or infection, as described. The peritoneal dialysate can be pumped through the fluid sensor apparatus 101 during a dwell period of a peritoneal dialysis cycle, or after the dwell period, during a drain portion of the peritoneal dialysis cycle. For example, the processor can be programmed to operate pump 103 and valves 107, 108, and 109 to remove a small amount of peritoneal dialysate from the patient at various times within a peritoneal dialysis cycle and pump the peritoneal dialysate through the fluid sensor apparatus 101. The valves 107, 108, and 109 can one-way, two-way, three-way, or n-way with any desired number of configuration. The sampling can take place at set times during a peritoneal dialysis cycle, such as every 15 minutes. Other set times, such as every 30 minutes, or every hour can also be used. The sampling can occur in any desired interval ranging from every minute to every hour. Other time intervals greater than one hour are contemplated and no restriction on time intervals is imposed. In certain embodiments, the system can allow a user to sample the peritoneal dialysate within the patient on demand. Alternatively, the peritoneal dialysate can be pumped through the fluid sensor apparatus 101 only at the end of a peritoneal dialysis cycle during draining of the peritoneal cavity. Using the fluid sensor apparatus 101 at the end of a peritoneal dialysis cycle may be advantageous because the markers detected by the fluid sensor apparatus 101 may not change rapidly during the intersession time period and the concentrations may be low enough to require testing during the drain portion of the cycle in order to accurately detect the markers.

As described, the fluid sensor apparatus 101 can detect one or more fluid characteristics in the spent peritoneal dialysate drained from the patient. In certain embodiments, the fluid sensor apparatus 101 can detect specific markers correlated with peritonitis or infection. The fluid sensor apparatus 101 can also detect additional fluid characteristics, including the pH of the spent peritoneal dialysate, as well as concentrations of one or more solutes, a color of the peritoneal dialysate, and/or a clarity of the peritoneal dialysate. A processor (not shown) in communication with the fluid sensor apparatus 101 can receive a signal from the fluid sensor apparatus 101 and identify or diagnose the patient with peritonitis and/or infection based on the received signal.

Figure 2A:
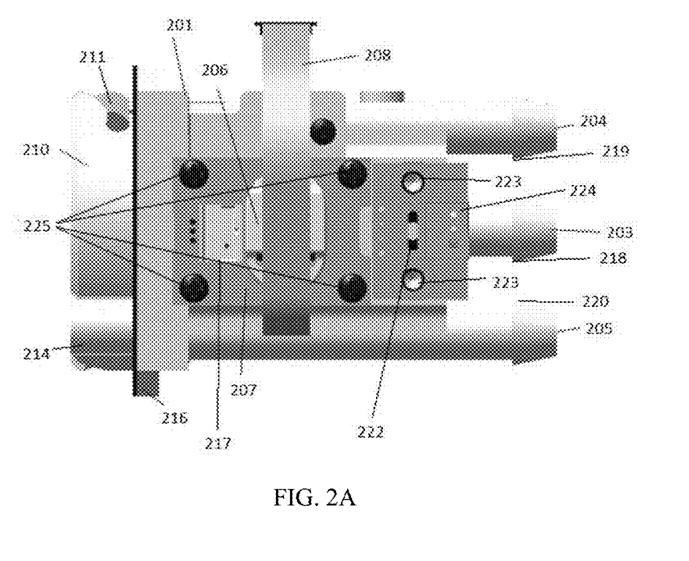
FIGS. 2A-F show a side, perspective, and top view of a fluid sensor apparatus.
Figure 2B:
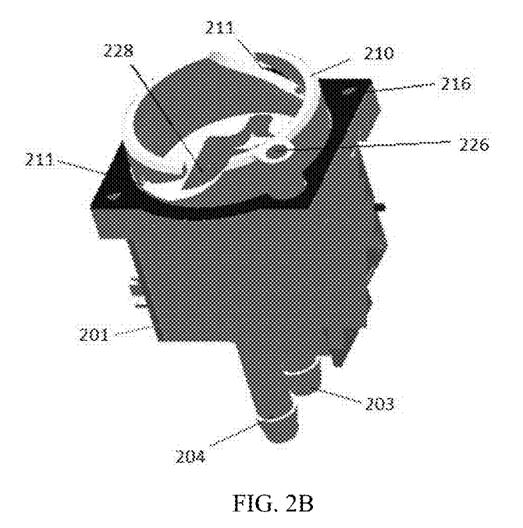
Figure 2C:
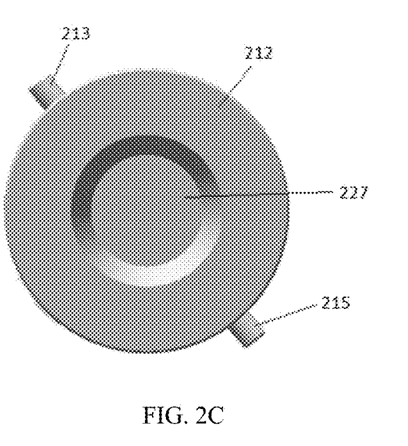
Figure 2D:
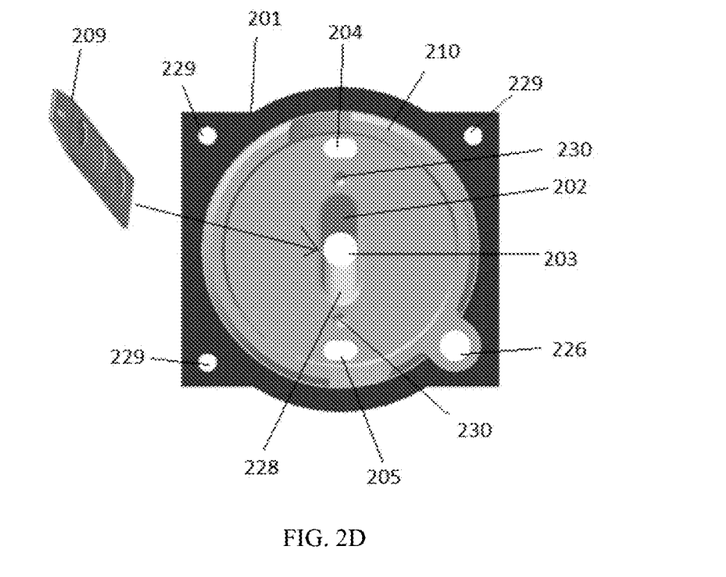
Figure 2E:
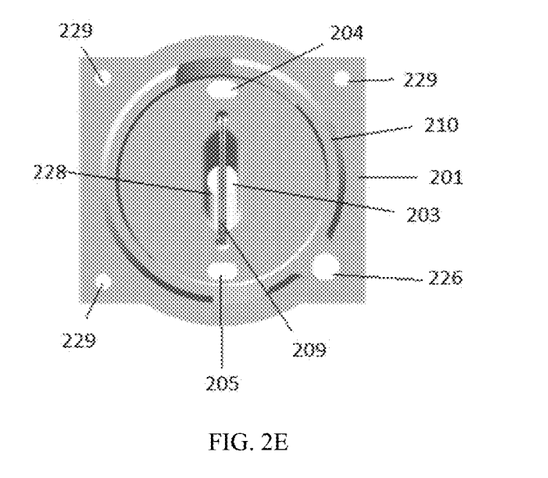
Figure 2F:
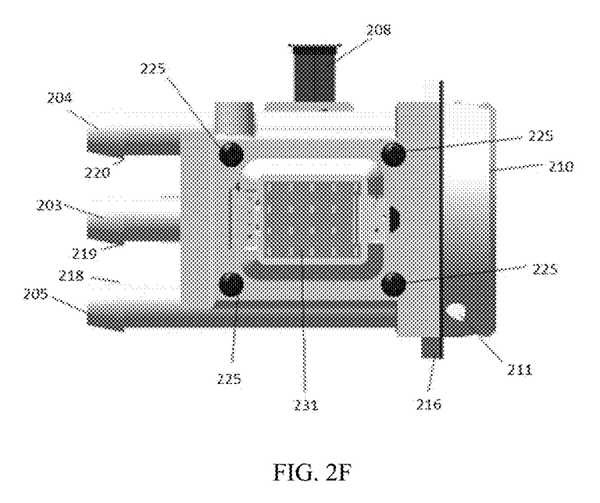

FIGS. 2A-F illustrate a non-limiting embodiment of a fluid sensor apparatus 201. FIG. 2A illustrates a side view of the fluid sensor apparatus 201; FIG. 2B illustrates a perspective view of the fluid sensor apparatus 201; FIG. 2C illustrates a receiving slot cover 212 for the fluid sensor apparatus 201; FIG. 2D illustrates a cut-away portion of the fluid sensor apparatus 201 at a specified depth and a sensor card 209 being inserted into a receiving slot 202 of the fluid sensor apparatus 201; FIG. 2E illustrates a front view of the fluid sensor apparatus 201 with the sensor card 209 inserted; and FIG. 2F illustrates a side view of the fluid sensor apparatus 201.

As shown in FIG. 2D, the fluid sensor apparatus 201 has a receiving slot 202 traversing a sampling chamber 228 along an axis. A removable sensor card 209 can be inserted into the receiving slot 202 as illustrated in FIGS. 2D and 2E to a specified depth of the fluid sensor apparatus 201. Indentations 230 on either side of the sampling chamber 228 at the depth of the fluid sensor apparatus 201 in FIG. 2D, can receive an edge of the sensor card 209, to seat or fasten the sensor card 209 in place. At a higher depth of the fluid sensor apparatus 201, a groove can be formed appurtenant to a sidewall of the sampling chamber 228 to receive a side edge of the sensor card 209. An edge of the sensor card 209 can be securely positioned in the sampling chamber 228 at a specified location or orientation with respect to a light source and/or photodetector. Alternatively, one or more grooves can be formed into the fluid sensor apparatus 201 to receive an edge of the sensor card 209 to securely position the sensor card 209 at a specified location or orientation if the sensor card 209 has a width greater than any axis of the sampling chamber 228 as shown in FIG. 2E.

Figure 3:
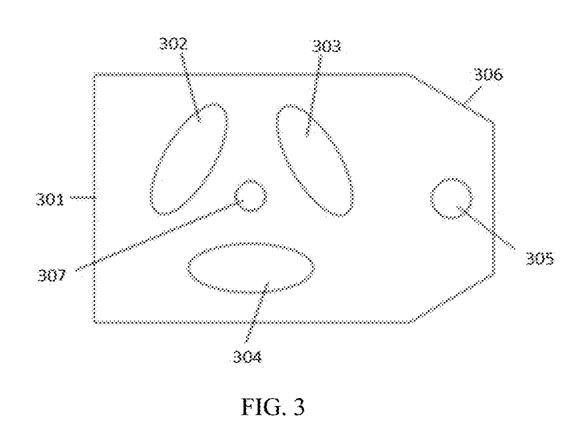
FIG. 3 illustrates a sensor card for use with the fluid sensor apparatus.

The sampling chamber 228 can have a plurality of clear windows on the sidewalls as shown in FIG. 3 to provide optical access to the sensor card 209. Holes 229 formed into the body of the fluid sensor apparatus 201 can be used to attach the fluid sensor apparatus 201 to a console or system using screws or other fasteners as shown in FIG. 2D. The sampling chamber 228 extends longitudinally along a length of the receiving slot 202 of the fluid sensor apparatus 201. The receiving slot 202 can extend beyond the sampling chamber 228 and terminate in a fastening mechanism to securely hold the sensor card 209, such as the indentation 230. The sampling chamber 228 can mix fluids to improve fluid contact on the sensor card 209. Notably, the sampling chamber 228 defines a volume such that a front side and a back side of the sensor card 209 can be exposed to fluid flow on both sides of the sensor card 209. The sampled fluid can therefore simultaneously contact a first and second side (or front and back) of the sensor card 209 to advantageously increase the surface area on which fluid contacts sensing membranes in the sensor card 209. The resulting mixing can result in improved sensing of the fluid by the sensor card 209 by making the response of the sensor card 209 to changes in the fluid faster.

The sensor card 209 can have at least one sensing membrane capable of detecting a marker correlated with peritonitis and/or an infection. Further, the sensor card 209 can include a pH sensing membrane to detect a pH of the fluid. The pH sensing membrane, the peritonitis or infection sensing membranes, or both, can change color, optical transmittance, or change emitted fluorescent light intensity or wavelength based on a pH or a concentration of a marker correlated with peritonitis or infection. The sensor card 209 can include a reference sensing region (not shown). The reference sensing region can be used to detect the color and/or clarity of the peritoneal dialysate in addition to, or as an alternative to, any of the other described fluid characteristics. Discolored or cloudy spent peritoneal dialysate can indicate an infection or peritonitis. Detecting the color or clarity of the spent peritoneal dialysate can determine whether the spent peritoneal dialysate includes any blood cells or discoloration, which may indicate peritonitis or infection. The reference sensing region may be a passive reference background color to which the photodetector or camera 206 can accurately detect the color and/or clarity of the fluid. The reference sensing region can be white, or any other solid color that can be detected by the photodetector or camera 206. The processor can compare the wavelength and/or intensity of light from the reference sensing region detected by the photodetector or camera 206 while fluid is pumped through the fluid sensor apparatus 201 as compared to a wavelength and/or intensity of light from the reference sensing region detected by the photodetector or camera 206 when water or any other clear fluid is pumped through the fluid sensor apparatus 201 to determine any changes in the color or clarity of the fluid.

However, the sensor card 209 is not limited to pH, peritonitis, or infection sensing membranes, and can include any colorimetric material producing a detectable change in response to a concentration or other fluid characteristic of a fluid. In general, the colorimetric material can produce any visible change such as change in color or optical transmittance, or a change in emitted fluorescent light intensity or wavelength, wherein the visible change is detected by the photodetector or camera 206 of the present invention. The sensor card 209 can also include only a pH sensing membrane, only a peritonitis or infection sensing membrane, or a sensing membrane having any type of colorimetric material.

As described, the color change of the one or more sensing membranes can be observed through the one or more clear windows positioned on the sidewall of the sampling chamber 228. The sensing membranes can be any material sensitive to a component of the fluid in the fluid path to be sensed. The sensing membrane has a property reacting to a fluid component that causes a detectable change in an optical parameter depending on the concentration of the component in the fluid or any other fluid characteristic. The optical parameter can be any one of color, reflectivity, transitivity fluorescence, adsorption, or any other parameter capable of being optically detected. In a preferred embodiment, the sensing membrane changes color in relationship to changes in the solute concentration of the measured fluid characteristic. For example, the membrane can change color in a first direction along a color spectrum as the solute concentration of the component in the fluid increases, and along a second direction as the solute concentration of the component decreases. The color change of the membrane can be continuous and reversible in response to the component concentration.

An optional temperature probe 222 can determine the temperature of the fluid within the fluid sensor apparatus 201. Along with specified markers, an elevated temperature can indicate an infection. Electrical connector 224 provides the electrical connection from the temperature probe 222 to the fluid sensor apparatus 201.

In FIG. 2F, one non-limiting example of a light source is shown as LED array 231 connected to the system by electrical connector 217. The LED array 231 can shine a light onto a first side of the sensor card 209 seated inside the receiving slot 202. The LED array 231 can direct light through the one or more clear windows in the sidewall of the sampling chamber 228. The light source can be any source of light at any wavelength capable of shining light onto the sensor card 209. In a preferred embodiment, the LED provides white light; however, any color or wavelength of light can be used. In a preferred embodiment, the light source provides uniform backlighting onto one side of the sensor card 209 such that a camera 206 (shown in FIG. 2A) positioned on an opposite side of the fluid sensor apparatus 201 can detect changes on an opposite side of the sensor card 209 via one or more clear windows. However, the LED array 231 can be positioned at any part of the apparatus capable of providing uniform light to the sensor card 209, including direct and side-firing or side-emitting LEDs. Importantly, light can be transmitted through the sensor card 209 and detected on an opposite side on which light is cast. In general, the clear windows for the LED array 231 and camera 206 can be antipodal to each other. The camera 206 can be any appropriate photodetector, spectrophotometer, or photosensor known to those of ordinary skill in the art. The camera 206 can transmit the image or sensed output to a processor for determining the pH and/or identifying the presence of infection or peritonitis and diagnosing the patient. The photodetector or camera 206 can also detect fluorescent light emitted from the sensor card 209. For detection of fluorescent light, an optical bandpass filter can be included in front of the camera 206 to allow the emitted fluorescent light to pass to the camera 206 while blocking any transmitted light from the LED array 231. The camera 206 can detect any change in the light transmitted including the wavelength of light, the mean intensity of light, the variation in intensity of light, and the pixel location in an image produced by the camera 206. Variation in intensity of light and pixel location allow the automatic detection of the sensor membrane position in the image captured by the photodetector or camera 206 for image analysis, making image analysis easier due to the known variations in intensity and location. A second LED array (not shown) or other light source can be included on the same side of the sensor card 209 as the camera 206 for illumination of a barcode or other identification component on the sensor card 209. The second LED array or light source can illuminate the identification component, which can then be read by the camera 206 to ensure the proper sensor card 209 is being used or to obtain data from the barcode or identification component.

In a preferred embodiment, the light is uniformly cast onto the sensor card 209. Such uniform lighting provided by an ordered arrangement of light sources can result in uniform or even backlighting onto the sensor card 209. The luminous intensity of the light on each sensing membrane can also be uniform, meaning that the power of the light emitted by the LED array 231 in each direction to each sensing membrane is uniform. The luminous flux, or the quantity of energy of the light transmitted onto each sensing membrane, can also be uniform, as can the illuminance, or luminous flux per area of the sensing membranes. The uniform lighting can be an ordered array of light sources, or a single homogenous light source that casts even lighting onto a surface. Diffuser films and a light cavity can also be included to provide uniform lighting. Diffuser films are thin films that evenly distribute transmitted light. Non-limiting examples of diffuser films include Brightness Enhancement Film (BEF), Dual Brightness Enhancement Film (DBEF), and Universal Diffuser Film 50 (UDF 50), available from 3M™, a Minnesota corporation. A light cavity is an arrangement of mirrors or other reflectors, such as white surfaces, that form standing waves from light. Advantageously, uniform backlighting can improve accuracy of the sensed color changes on the sensor card 209. The clear windows can be similarly positioned uniformly or in a pattern on the sidewalls to receive the uniform light dispersion. For example, the lights on the LED array 231 can be arranged in any shape, including rectangular, circular, or other shape, to cast light onto the sensor card 209 in a desired dispersion. The sensing membranes can then be positioned on the sensor card 209 to align with light cast by the LED array 231. Further, the power supply for the LED array 231 can provide a stable current and voltage to increase light uniformity.

Although illustrated as opposing the camera 206, the LED array 231 can be positioned anywhere on the fluid sensor apparatus 201, including on any side of the fluid sensor apparatus 201. A light guide can be included to allow light from an LED array 231 positioned on a side of the fluid sensor apparatus 201 to be transmitted through the sensor card 209 and onto the camera 206 along any reflectance pathway. For example, a mirror arrangement can guide light to a photodetector or camera 206 such that the photodetector or camera 206 need not be in directly positioned opposite to the light source. The light guide can provide a reflectance pathway such that the photodetector or camera 206 can be positioned in any convenient location to receive the reflected light. Similarly, the LEDs or any light source can rely on a light guide to direct light such that light sources can be conveniently positioned at any position and need not be opposedly positioned to the photodetector or camera 206. In one embodiment, both the light source and the photodetector or camera 206 transmit and receive light, respectively, using a light guide. The backlight settings can be computer controlled to optimize the backlight for each sensor membrane. The light from the LED array 231 can be set at a first intensity, optimized for a first sensor membrane. The LED can then be switched to a second intensity, optimized for a second sensor membrane. The camera 206 can take an image of each sensor membrane at the optimized backlighting.

In FIGS. 2A and F, the camera 206 and LED array 231 can be placed on opposing sides of the receiving slot 202 to help reduce hot spots formed on the sensor card 209. The light source shown as the LED array 231 and the photo camera described as camera 206 can be positioned opposite to each other on a line or plane that is substantially orthogonal to the receiving slot 202 containing the sensor card 209. A grating light valve (not shown) having an adjustable diffraction grating can be included to control the intensity of light diffracted onto the camera 206. The diffraction grating can be a set of equally spaced, narrow, parallel grates. The grates can disperse the light at different wavelengths, so that light intensity can be measured as a function of a particular wavelength. One or more light diffusive layers can also be included to diffuse the light shining on the sensing material of the sensor card 209 prior to detection by the camera 206. The clear windows can be free from scratches that degrade the sensor performance. In one non-limiting embodiment, to reduce scratches to the clear windows, the windows can be solvent polished. As shown in FIG. 2F, the camera 206 can transmit the image or other sensed output to a processor (not shown) in electronic communication with the camera 206 via electronic link 208.

As described, the processor can determine the color of the pH sensing membrane and/or marker sensing membrane to determine the pH and/or presence of peritonitis or infection, or the concentration of any solutes or ions, in the fluid flowing through the fluid sensor apparatus 201 based on the sensed output. Electronics 207 of FIG. 2A can control the camera 206 and the light source. Although illustrated as having wired communication links between the camera 206, electronics 207, and processor, one of skill in the art will understand that any method of transmitting and receiving data can be used, including Bluetooth, Wi-Fi, or any other methods known in the art. The processor can receive data, and in particular, the image produced by the camera 206, and determine the intensity of the pixels of a particular color in an image of the sensing membranes. The processor can determine the intensity of a specific color of pixels, such as green pixels, in the image produced by the camera 206. However, other colors such as red, blue, or any other suitable color can be used. The definitions of red, green, and blue light can be based on the camera operating software or can be specified by a controller or operating control logic. A spectrophotometer, which measures the wavelength and intensity of the transmitted light can also be used. Advantageously, a spectrophotometer can be more specific to a color of light detected. The processor can then determine the pH, and/or the levels of markers correlated with peritonitis or infection. The processor can use lookup tables, algorithms or any other method for correlating the number of color pixels in the image produced by the camera 206 to a fluid characteristic. The processor can be housed within, or positioned outside of, the fluid sensor apparatus 201. The camera 206 can be operated under manual control or by a software application for controlling the exposure, gain and white balance.

As shown in FIG. 2A, fluid can enter the fluid sensor apparatus 201 through a fluid inlet 203 and into the sampling chamber 228 of FIG. 2D. The fluid contacts the sensor card 209 seated in the receiving slot 202 of the sampling chamber 228. The fluid can then exit the sampling chamber 228 through fluid outlets 204 and 205. The fluid outlets 204 and 205 and the fluid inlet 203 can be both positioned on the same side of the sampling chamber 228 to provide a curved fluid flow path such that fluid can enter through the fluid inlet 203 positioned in between fluid outlets 204 and 205 wherein fluid then flows into a first end of the sampling chamber 228 and flows in a curved flow path and out a second end of the sampling chamber 228 and into the two fluid outlets 204 and 205 positioned on the same side as the sampling chamber 228. Conversely, the two fluid outlets 204 and 205 can be used as inlets to introduce fluid into sampling chamber 228 along a curved flow path such that fluid flows into and out of the fluid inlet 203. One of skill in the art will understand that one or more fluid inlets and outlets can be used. In a preferred embodiment, the two fluid outlets 204 and 205 advantageously improve fluid contact of the sensing membrane of the sensor card 209. Notch 218 on fluid inlet 203, notch 219 on outlet 204, and notch 220 on outlet 205 can provide secured fastening of the fluid inlet 203 and fluid outlets 204 and 205 to tubing as needed.

In FIG. 2C, the receiving slot 202 can include additional components to ensure that the detachable receiving slot cover 212 fits tightly over the receiving slot 202 and does not move as fluid is flowed into and through the sampling chamber 228. As illustrated in FIGS. 2A and 2B, the receiving slot 202 can have an extended portion 210 that will contact the receiving slot cover 212 when closed. The extended portion 210 can include grooves 211 and 214 for receiving pins 213 and 215 when the receiving slot cover 212 is placed over the receiving slot 202. The pins 213 and 215 engage with the grooves 211 to ensure the receiving slot cover 212 is properly placed and securely fastened on the fluid sensor apparatus 201.

To improve accurate measurements, the sensor card 209 can be fixed into a specified position and/or orientation inside the receiving slot 202 to resist any movement due to the flow of the fluid. Any suitable fastener to fix the receiving slot cover 212 to the fluid sensor apparatus 201 is contemplated. Magnets can be placed within the receiving slot cover 212 and the fluid sensor apparatus 201 to determine whether the receiving slot cover 212 is in the proper position. If the receiving slot cover 212 is closed, the magnets can provide a means to determine if receiving slot cover 212 is closed over the receiving slot 202 on the fluid sensor apparatus 201. As shown in FIG. 2F, overhang 216 can provide support for the receiving slot cover 212 when closed. In FIGS. 2D and 2E, opening 226 on extended portion 210 can provide for a fastener to be inserted through the receiving slot cover 212 to secure the receiving slot cover 212 onto the fluid sensor apparatus 201.

In FIG. 2C, an annular bevel 227 can be formed on the receiving slot cover 212 to capture the sensor card 209 and hold the sensor card 209 securely locked in the fluid sensor apparatus 201. Screws 225 fasten the electronics 207 and camera 206 to the fluid sensor apparatus 201. Alternative methods of securing components to the fluid sensor apparatus 201 can be used, including adhesive, glue, bolts, or any other securing components known in the art. Holes 223 allow additional components and electronics to be added to the fluid sensor apparatus 201.

FIG. 3 illustrates a non-limiting embodiment of a sensor card 301 for use with the fluid sensor apparatus. The sensor card 301 can have three sensing membranes containing a colorimetric material. The sensing membranes can include any colorimetric material, including a first sensing membrane 302 for detection of a first marker correlated with peritonitis or infection, a second sensing membrane 303 for detection of a first marker correlated with peritonitis or infection, and a pH sensing membrane 304. The sensor card 301 can also include a reference sensing region 307. One of skill in the art will understand that any number of sensing membranes can be included in the sensor card 301, including 1, 2, 3, 4, 5, 6, or more sensing membranes of any type. Multiple sensing membranes of the same type can provide redundancy and further accuracy. As described, the sensor card 301 can include a hole 305 for equalizing pressure when fluid is flowed across both sides of the sensor card 301. The sensor card 301 can also have at least one tapered edge 306. As described, the tapered edge 306 can fit within a bevel in the receiving slot or receiving slot cover of the fluid sensor apparatus, further fixing the sensor card 301 in place. Although shown as a circular array of sensing regions in FIG. 3, the sensor card 301 can include any type of array of sensing regions, including a linear array of sensing regions, as illustrated with sensor card 209 in FIGS. 2A-F.

As described, the sensor card 301 can include one or more sensing membranes 304 that can be used to detect peritonitis or infection. Non-limiting examples markers correlated with peritonitis or infection include materials that can cause a sensing membrane to produce a visual change include MMP8, IL-6, HNE, MMP2, MMP9, TIMP1, TIMP2, NGAL, A1AT, desmosine, fibrinogen, IL-8, calprotectin, fMLP, IL1 b, cystatin C, HSA, RBP4, SPD, MPO, sICAM and TNFa. One of skill in the art will understand that additional markers can be correlated with peritonitis and infection that may be detected by the described fluid sensor apparatus.

Each of the markers can be detected using an enzyme linked immunosorbent assay (ELISA) technique or any other known technique known to those of ordinary skill. Antigens or capture molecules specific for a marker correlated with peritonitis or infection can be immobilized in a sensing region of the sensor card. A reporter molecule, typically an antibody or fragment or derivative thereof, can be contained in the sensor card. The reporter molecule interacts with the marker if present and bound in the sensor region. The reporter molecule becomes immobilized in the sensor region when the marker is present and can produce a detectable change in the sensor region upon immobilization. As described, the fluid sensor apparatus can detect the change in color, optical transmittance, or change emitted fluorescent light intensity or wavelength resulting from the binding of the reporter molecule, and thereby detect the presence or concentration of the marker in peritoneal dialysate pumped through the fluid sensor apparatus.

Figure 4:
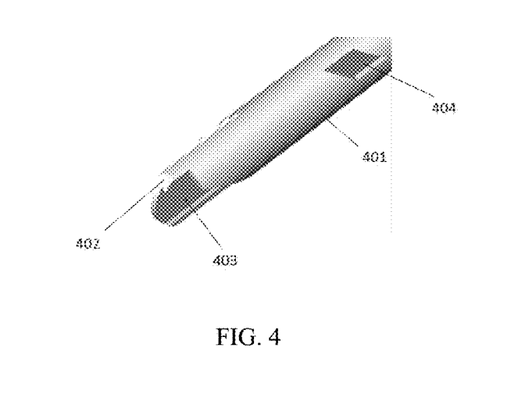
FIG. 4 illustrates a non-limiting example of a catheter for use with the peritoneal dialysate fluid testing system.

As described, any type of peritoneal dialysis catheter can be used with the peritoneal dialysate fluid testing system. One non-limiting example is the Palindrome™ catheter, available from Medtronic Inc., an Irish corporation, illustrated in FIG. 4. A tip 402 of the catheter 401 is inserted into the peritoneal cavity of a patient. As illustrated in FIG. 4, the catheter 401 can be a dual-lumen catheter, with a first lumen 403 for moving fluid into the patient, and a second lumen (not shown in FIG. 4) for removing fluid from the patient. One or more side slots 404 can be present to promote flow over the surface of the catheter 401, minimizing debris attachment and lessening the risk for clot formation. The catheter 401 can be fluidly connectable to a drain line including the fluid sensor apparatus illustrated in FIGS. 1-2. Peritoneal dialysate can be withdrawn from a patient through the catheter 401 and through a drain line to the fluid sensor apparatus for detection and diagnosis of peritonitis or infection.

Although illustrated in FIG. 4 as a dual lumen catheter 401 with side slots 404, one of skill in the art will understand that alternative catheters are contemplated. Further, the system can use a mono-lumen catheter, a tri-lumen catheter or any type of multi-lumen catheter. With tri- or multi-lumen catheters, one of the lumens can be dedicated for sampling to a sensor line, which can contain the fluid sensor apparatus and/or any other described sensors. Any catheter with or without side slots or side holes can be used with the peritoneal dialysate fluid testing system.

It will be apparent to one skilled in the art that various combinations and/or modifications and variations can be made in the dialysis system depending upon the specific needs for operation. Moreover, features illustrated or described as being part of an aspect of the invention can be included in the aspect of the invention, either alone or in combination.

We claim:

1. A system, comprising:
a peritoneal dialysis cycler; the peritoneal dialysis cycler comprising a catheter for removing peritoneal dialysate from a patient, at least one fluid line fluidly connected to the catheter, and a pump;
a fluid sensor apparatus; the fluid sensor apparatus fluidly connected to the fluid line; the fluid sensor apparatus detecting at least one fluid characteristic in fluid removed from the patient; and a processor, the processor programmed to identify peritonitis and/or infection based on the at least one fluid characteristic;
wherein the fluid sensor apparatus comprises:
at least one fluid inlet fluidly connected to the fluid line and at least two fluid outlets fluidly connected to a second fluid line;
a receiving slot for a sensor card; the receiving slot fluidly connected to the fluid inlet and fluid outlet;
wherein the at least one fluid inlet fluidly connects the receiving slot to the first fluid line; and wherein each of the at least two fluid outlets fluidly connect the receiving slot to the second fluid line.

2. The system of claim 1, wherein the at least one fluid characteristic comprises at least one marker correlated with peritonitis and/or infection.

3. The system of claim 1, wherein the fluid sensor apparatus comprises:
a light source directing light onto a first side of the sensor card; and
a camera or photodetector detecting light on a second side of the sensor card opposite to the first side of the sensor card;
the camera or photodetector in communication with a processor, the processor programmed to identify peritonitis and/or infection based on the at least one fluid characteristic.

4. The system of claim 3, wherein the sensor card comprises at least one sensor region; the at least one sensor region undergoing a detectable change in response to at least one marker correlated with peritonitis and/or infection.

5. The system of claim 3, wherein the sensor card comprises at least two sensor regions; wherein a first sensor region undergoes a detectable change in response to a first marker correlated with peritonitis and/or infection; and wherein a second sensor region undergoes a detectable change in response to a second marker correlated with peritonitis and/or infection.

6. The system of claim 4, wherein the at least one marker is selected from a group consisting of MMP8, IL-6, HNE, MMP2, MMP9, TIMP1, TIMP2, NGAL, A1AT, desmosine, fibrinogen, IL-8, calprotectin, fMLP, IL1 b, cystatin C, HSA, RBP4, SPD, MPO, sICAM and TNFa.

7. The system of claim 3, further comprising a bypass line fluidly connecting the fluid line upstream of the fluid sensor apparatus to the second fluid line downstream of the fluid sensor apparatus.

8. The system of claim 3, wherein the second fluid line is fluidly connected to a drain and/or to a waste reservoir.

9. The system of claim 1, wherein the catheter is a dual lumen catheter.

10. The system of claim 9, the catheter comprising at least one side slot.

11. The system of claim 1, wherein the at least one fluid characteristic on which the processor is programmed to identify peritonitis and/or infection comprises at least one of a color and a clarity of the fluid.

* * * * *